US012773514B2

(12) United States Patent
Orr et al.

(10) Patent No.: US 12,773,514 B2
(45) Date of Patent: *Oct. 27, 2026

(54) APPARATUS FOR CONNECTING OXYGEN DELIVERY CONTROL INSTRUMENT TO PATIENT DELIVERY DEVICE

(71) Applicant: Dynasthetics, LLC, Salt Lake City, UT (US)

(72) Inventors: Joseph Orr, Park City, UT (US); Kyle M. Burk, Farmington, UT (US); Eric Youngberg, Layton, UT (US); Derek Sakata, Salt Lake City, UT (US)

(73) Assignee: Dynasthetics, LLC, Salt Lake City, UT (US)

( * ) Notice: Subject to any disclaimer, the term of this patent is extended or adjusted under 35 U.S.C. 154(b) by 454 days.

This patent is subject to a terminal disclaimer.

(21) Appl. No.: 18/516,050

(22) Filed: Nov. 21, 2023

(65) Prior Publication Data

US 2024/0082528 A1 Mar. 14, 2024

Related U.S. Application Data

(63) Continuation of application No. 16/925,016, filed on Jul. 9, 2020, now Pat. No. 11,819,621, which is a
(Continued)

(51) Int. Cl.
*A61M 16/08* (2006.01)
*A61M 16/00* (2006.01)

(52) U.S. Cl.
CPC ...... *A61M 16/0875* (2013.01); *A61M 16/022* (2017.08); *A61M 16/085* (2014.02);
(Continued)

(58) Field of Classification Search
CPC ... A61H 1/008; A61M 11/00; A61M 16/0051; A61M 16/022; A61M 16/024; A61M 16/0672; A61M 16/0816; A61M 16/085; A61M 16/0858; A61M 16/0875; A61M 2016/0027; A61M 2016/003;
(Continued)

(56) References Cited

U.S. PATENT DOCUMENTS 4,306,743 A 12/1981 Hinshaw et al.
6,126,610 A 10/2000 Rich et al.
(Continued)

FOREIGN PATENT DOCUMENTS

EP 1731188 B1 10/2012
WO 2014164813 A1 10/2014

OTHER PUBLICATIONS

Extended European Search Report dated Dec. 22, 2020 from related European application EP 20 18 8280.

*Primary Examiner* — Annette Dixon
(74) *Attorney, Agent, or Firm* — Dentons Durham Jones Pinegar; Sarah W. Matthews; Lilly Godfrey

(57) ABSTRACT

A connector for connecting an oxygen delivery device to a patient interface. The connector includes a housing with a first lumen for delivering oxygen and a second lumen to allow pressure to be measured. A third optional lumen may allow for gas sampling. The housing surrounding the first and second lumen has a portion that includes encoding for determining the type of patient interface being used, as well as a depth indicator sensor.

19 Claims, 5 Drawing Sheets

Related U.S. Application Data continuation of application No. 16/532,248, filed on Aug. 5, 2019, now Pat. No. 10,737,049.

(52) U.S. Cl.
CPC ... *A61M 16/0858* (2014.02); *A61M 2016/003* (2013.01); *A61M 2202/0208* (2013.01); *A61M 2205/14* (2013.01); *A61M 2205/3306* (2013.01)

(58) Field of Classification Search
CPC .. A61M 2039/1027; A61M 2039/1083; A61M 2039/1088; A61M 2202/0007; A61M 2202/0208; A61M 2205/14; A61M 2205/18; A61M 2205/3306; A61M 2205/3313; A61M 2205/50; A61M 2205/6018; A61M 2205/6036; A61M 2205/6045; A61M 2205/6063; A61M 2230/432; A61M 2240/00; A61M 39/12; F16L 37/56; F16L 39/02; Y10T 403/1616
See application file for complete search history.

(56) References Cited

U.S. PATENT DOCUMENTS

| | | | | |
|---|---|---|---|---|
| 7,086,422 | B2 | 8/2006 | Huber et al. | |
| 7,762,253 | B2 | 7/2010 | Acker et al. | |
| 8,092,409 | B2 | 1/2012 | Mros et al. | |
| 9,919,124 | B2 * | 3/2018 | Ahmad | A61M 16/0833 |
| 10,143,820 | B2 | 12/2018 | Orr | |
| 10,159,815 | B2 | 12/2018 | Orr | |
| 10,737,049 | B1 * | 8/2020 | Orr | A61M 16/024 |
| 11,819,621 | B2 * | 11/2023 | Orr | A61M 16/0858 |
| 2002/0124845 | A1 | 9/2002 | Lauer | |
| 2005/0184264 | A1 | 8/2005 | Tesluk et al. | |
| 2007/0144519 | A1 | 6/2007 | Henry et al. | |
| 2015/0306332 | A1 | 10/2015 | Bafile et al. | |

* cited by examiner

APPARATUS FOR CONNECTING OXYGEN DELIVERY CONTROL INSTRUMENT TO PATIENT DELIVERY DEVICE

CROSS-REFERENCE TO RELATED MATTER

This application is a continuation of U.S. patent application Ser. No. 16/925,016, filed Jul. 9, 2020 and titled APPARATUS FOR CONNECTING OXYGEN DELIVERY CONTROL INSTRUMENT TO PATIENT DELIVERY DEVICE ("the '016 application"), now U.S. Pat. No. 11,819,621, issued Nov. 21, 2023 which is a continuation of U.S. patent application Ser. No. 16/532,248, filed Aug. 5, 2019 and titled APPARATUS FOR CONNECTING OXYGEN DELIVERY CONTROL INSTRUMENT TO PATIENT DELIVERY DEVICE ("the '248 application"), now U.S. Pat. No. 10,737,049, issued Aug. 11, 2020. The entire disclosure of the '016 Application and the '248 application are hereby incorporated herein by reference.

TECHNICAL FIELD

The present disclosure relates generally to a system and method to deliver oxygen to a patient from an oxygen delivery control device to a patient interface. More specifically, the present disclosure relates to a method and apparatus for connecting a patient interface and an oxygen delivery control device.

BACKGROUND

Oxygen is often supplied to patients during medical procedures. Known methods for regulating oxygen supply may provide increased benefits for patient safety. Such systems are disclosed, for example, in U.S. Pat. Nos. 10,159,815 and 10,143,820, which are incorporated herein in their entireties. Many respiratory systems are characterized by complexity and diversity of possible applications. Often, a plurality of components must be connected before a respiratory system is used.

Different interfaces usually have to be connected using means of connection, and in some cases this can give rise to an increased risk of error and possibly cause a dangerous situation for a patient. A standard connection from a patient interface, such as a nasal cannula or a CPAP mask, for example, may be provided to the oxygen delivery device or respiratory system. Risks of incorrect connection include both a wrong connection and an incomplete connection (that is, the connection is only partial, and the patient is not delivered sufficient oxygen as a result). An incomplete connection may occur with partial insertion, or if a connector is inserted fully and then later becomes partially dislodged.

It may be advantageous, therefore, to provide a connector to reduce the risk of incorrect connections and/or partial connections.

SUMMARY OF DISCLOSURE

A connector for connecting a patient interface to an oxygen delivery control device may include a first lumen for conveying pressurized oxygen from a pressurized oxygen source in connection with the oxygen delivery control device to the patient interface. The connector may also include a second lumen for measuring patient breath pressure, the second lumen having a smaller diameter than the first lumen. In some embodiments, the first and second lumens are enclosed in a housing, with the housing having a top surface, the top surface comprising a first top surface portion and a second top surface portion. The first top surface portion may have a larger width than a width of the second top surface portion, and an open slot in the top surface of the housing may separate the first top surface portion and the second top surface portion. In some embodiments, the open slot is configured to receive an optical isolation wall of the oxygen delivery control device. The first top surface portion of the housing may comprise at least one encoding optical reflectivity pad configured to enable identification of information relating to the patient interface. The second top surface portion of the housing may comprise a chamfer proximal to the open slot, with the chamfer configured to enable measurement of a depth of the housing within the oxygen delivery control device.

The first lumen may be configured to receive a standard clinical oxygen barb connector, whereas the second lumen cannot receive a standard clinical oxygen barb connector.

In some configurations, the information relating to the patient interface comprises a type of patient interface and/or size of patient interface. The type of patient interface may be selected from at least one of a nasal cannula, a CPAP mask, an auxiliary oxygen tube, and a drug nebulizer. The size of the patient interface may be selected from at least one of adult, pediatric, and neonatal.

According to another aspect, the at least one encoding optical reflectivity pad may be configured to cause a software constraint relating to maximum oxygen flow when the at least one encoding optical reflectivity pad is inserted into the oxygen delivery control device.

According to another aspect, a third lumen may be provided in the connector. The third lumen may have a diameter smaller than the diameter of the first lumen. The third lumen may be for drawing a sample of gas for analysis, for example, exhaled CO 2 concentration analysis.

According to another aspect, the first and second lumens are formed from a flexible material, while the housing may be formed of a rigid material.

According to another aspect, a connector is described herein, the connector including a housing having a top surface extending from a first side to a second side, with the top surface comprising a patient interface encoding portion and a depth measurement insertion portion. In some embodiments, an open slot in the top surface of the housing separates the patient interface encoding portion and the depth measurement insertion portion. The patient interface encoding portion of the housing may comprise means to enable identification of information relating to the patient interface. The depth measurement insertion portion of the housing may comprise means to enable measurement of a depth of the housing within the oxygen delivery control device. In some embodiments, housing encloses a first lumen and a second lumen, with the first lumen for conveying pressurized oxygen and the second lumen for measuring of intra-nasal pressure at the patient interface, the second lumen having a smaller diameter than the first lumen.

In some configurations, the open slot may be positioned closer to the second side of the housing. In some configurations, the means to enable identification of information relating to the patient interface comprises means for optical detection, for example, at least two reflective pads, the at least two reflective pads configured to reflect infrared light at one of high reflectivity, low reflectivity, and intermediate reflectivity.

According to another aspect, the means to enable detection of a depth of the housing within the oxygen delivery control device comprises at least one of: a triangle printed on the depth insertion portion, a gradient printed on the depth insertion portion, an angled cut-away formed in the depth insertion portion, and a reflective pad placed on the depth insertion portion. The means to enable detection of a depth of the housing within the oxygen delivery control device, in some configurations, comprises a continuously variable reflective pad. In some configurations, a third lumen may be provided to enable end-tidal CO 2 measurement, the third lumen having a diameter smaller than the diameter of the first lumen.

According to yet another aspect, a system for delivering oxygen to a patient may include a patient interface and an oxygen delivery control device comprising a receptacle with an optical isolation wall formed therein. The system may additionally include a connector for connection the patient interface to the oxygen delivery control device, with the connector comprising a first lumen for conveying pressurized oxygen from a pressurized oxygen source in connection with the oxygen delivery control device to the patient interface and a second lumen for measuring pressure at the patient interface. In some embodiments, the second lumen has a smaller diameter than the first lumen. They first and second lumens may be enclosed in a housing, the housing having a top surface, with the top surface comprising a first top surface portion and a second top surface portion. The first top surface portion may have a larger width than a width of the second top surface portion, and an open slot in the top surface of the housing may separate the first top surface portion and the second top surface portion. In some embodiments, the open slot is configured to receive the optical isolation wall of the oxygen delivery control device. The first top surface portion of the housing may comprise at least one encoding optical reflectivity pad configured to enable identification of information relating to the patient interface. The second top surface portion of the housing may comprise a chamfer proximal to the open slot, the chamfer configured to enable measurement of a depth of the housing within the oxygen delivery control device.

In some configurations, the at least one encoding optical reflectivity pad is configured to cause a software constraint relating to maximum oxygen flow when the at least one encoding optical reflectivity pad is inserted into the oxygen delivery control device. The software constraint may include, for example, one of a maximum oxygen flow, a minimum oxygen flow, a minimum mask pressure, a minimum mask pressure, and a maximum oxygen pulse frequency.

According to yet another aspect, a method is disclosed for connecting a patient interface to an oxygen delivery control device, the method comprising selecting the connector as described herein and selecting the oxygen delivery control device, the oxygen delivery control device comprising a receptacle to receive at least a portion of the housing of the connector, with the receptacle having an isolation wall formed therein. The oxygen delivery control device may further comprise at least two optical sensors proximal to the receptacle. The method may include inserting the housing of the connector into the receptacle of the oxygen delivery control device. In some configurations, the method may also include the steps of a first optical sensor identifying information relating to the patient interface based on the at least one encoding optical reflectivity pad, and a second optical sensor measuring the depth of the housing within the receptacle.

BRIEF DESCRIPTION OF DRAWINGS

The following drawings illustrate what are currently considered to be specific representative configurations for carrying out the invention and are not limiting as to embodiments which may be made in accordance with the present invention. The components in the drawings are not necessarily to scale relative to each other. Like reference numerals designate corresponding parts throughout the several views.

The drawings are illustrative and not limiting of the scope of the invention which is defined by the appended claims. The various elements of the invention accomplish various aspects and objects of the invention. Not every element of the invention can be clearly displayed in a single drawing, and as such not every drawing shows each element of the invention.

DETAILED DESCRIPTION

Figure 1:
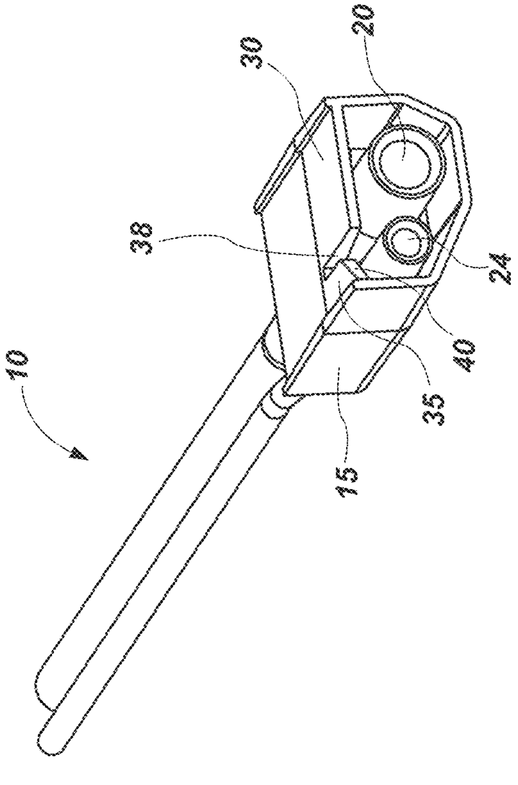
FIG. 1 shows a perspective view of a connector as described herein for connecting a patient interface to an oxygen delivery control device.

The following provides a detailed description of particular embodiments of the present invention. Reference will now be made to the drawings in which the various elements of the illustrated configurations will be given numerical designations and in which the invention will be discussed so as to enable one skilled in the art to make and use the invention. It is to be understood that the following description is only exemplary of the principles of the present invention, and should not be viewed as narrowing the scope of the claims which follow, which claims define the full scope of the invention.

It will be appreciated that various aspects discussed in one drawing may be present and/or used in conjunction with the embodiment shown in another drawing, and each element shown in multiple drawings may be discussed only once. For example, in some cases, detailed description of well-known items or repeated description of substantially the same configurations may be omitted. This facilitates the understanding of those skilled in the art by avoiding an unnecessarily redundant description. The accompanying drawings and the following description are provided in order for those skilled in the art to fully understand the present disclosure, and these are not intended to limit the gist disclosed in the scope of claims.

It should be noted that the description merely illustrates the principles of the present subject matter. It will thus be appreciated that those skilled in the art will be able to devise various arrangements that, although not explicitly described herein, embody the principles of the present subject matter and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

Reference in the specification to "one configuration" "one embodiment," "a configuration" or "an embodiment" means that a particular feature, structure, or characteristic described in connection with the configuration is included in at least one configuration, but is not a requirement that such feature, structure or characteristic be present in any particular configuration unless expressly set forth in the claims as being present. The appearances of the phrase "in one configuration" in various places may not necessarily limit the inclusion of a particular element of the invention to a single configuration, rather the element may be included in other or all configurations discussed herein.

Furthermore, the described features, structures, or characteristics of configurations of the invention may be combined in any suitable manner in one or more configurations. In the following description, numerous specific details are provided, such as examples of products or manufacturing techniques that may be used, to provide a thorough understanding of configurations of the invention. One skilled in the relevant art will recognize, however, that configurations of the invention may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present disclosure is not limited to any particular structures, process steps, or materials discussed or disclosed herein, but is extended to include equivalents thereof as would be recognized by those of ordinary skill in the relevant art. More specifically, the invention is defined by the terms set forth in the claims. It should also be understood that terminology contained herein is used for the purpose of describing particular aspects of the invention only and is not intended to limit the invention to the aspects or configurations shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, reference to "a micro controller" may include one or more of such microcontrollers, and reference to "the sensor" may include reference to one or more of such sensors.

As used herein, the term "substantially" refers to the complete or nearly complete extent or degree of an action, characteristic, property, state, structure, item, or result to function as indicated. For example, an object, such as a reflectivity pad, that is "substantially" continuously variable would mean that the object is either completely continuously variable or nearly completely continuously variable. The use of "substantially" is equally applicable when used in a negative connotation to refer to the complete or near complete lack of an action, characteristic, property, state, structure, item, or result.

As used herein the term "generally" refers to something that is more of the designated adjective than not, or the converse if used in the negative.

As used herein, the term "about" is used to provide flexibility to a numerical range endpoint by providing that a given value may be "a little above" or "a little below" the endpoint while still accomplishing the function associated with the range.

As used herein, a plurality of items, structural elements, compositional elements, and/or materials may be presented in a common list for convenience. However, these lists should be construed as though each member of the list is individually identified as a separate and unique member.

Concentrations, amounts, proportions and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

It should be noted that the description merely illustrates the principles of the present subject matter. It will thus be appreciated that those skilled in the art will be able to devise various arrangements that, although not explicitly described herein, embody the principles of the present subject matter and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

The manner in which the systems and methods may be implemented is explained in details with respect to the figures. While aspects of described systems and methods can be implemented in any number of different computing systems, transmission environments, and/or configurations, the embodiments are described in the context of the following exemplary system(s).

It will also be appreciated by those skilled in the art that the words during, while, and when as used herein are not exact terms that mean an action takes place instantly upon an initiating action but that there may be some small but reasonable delay, such as a propagation delay, between the initial action and the reaction that is initiated by the initial action. Additionally, the word "connected" and "coupled" is used throughout for clarity of the description and can include either a direct connection or an indirect connection. As used herein, "lumen" refers to a generally hollow tubular structure.

Figure 2:
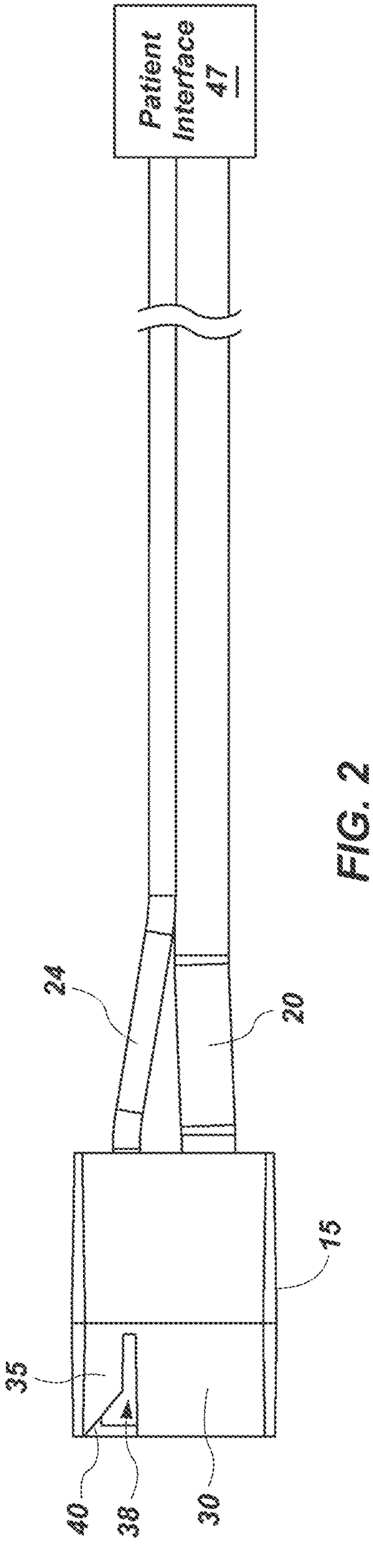
FIG. 2 shows a top, plan view of the connector of FIG. 1, attached to a patient interface shown in diagrammatic view.

The present disclosure relates generally to a connector for connecting an oxygen delivery system to a specific patient interface. One particular embodiment of the present disclosure is shown and described in the connector of FIGS. 1-2. The connector 10 of may include a patient interface 47 on one end (FIG. 2), and a housing 15 on the other end configured to be plugged into an oxygen delivery control device. The connector 10 may include a housing 15 that encloses a first lumen 20 and a second lumen 24. The first lumen 20 may be configured to convey pressurized oxygen from a pressurized oxygen source in connection with the oxygen delivery control device to the patient interface. In addition to being able to connect with the oxygen delivery control device, the first lumen 20 may also be sized to connect directly to a standard clinical oxygen barb connector. For example, the first lumen 20 or oxygen lumen may have an inner diameter of about 5 mm to about 6.35 mm (about 0.2" to about 0.25" inner diameter). In other configurations, the first lumen 20 may have an inner diameter of about 4 mm to about 8 mm.

The second lumen 24 may be provided for measuring patient breath pressure. Patient breath pressure may depend on the type of patient interface used. For example, patient breath pressure may be nasal pressure, breathing mask pressure, patient airway pressure, etc. In some configurations, the second lumen 24 may be smaller than the first lumen 20, such that the second lumen 24 cannot be plugged into a standard clinical oxygen barb connector. For example, the second lumen 24 may have an inner diameter of less than 5 mm (or less than 0.14"). In some configurations, the second lumen 24 may have an inner diameter of about 3 mm to about 4 mm.

Each of the first and the second lumens 20, 24 may be formed of a flexible material. For example, flexible PVC may be used (such as Geon HC, by PolyOne Corp., or any other suitable flexible material known in the art). The flexible material may allow the first lumen 20 to be connected/stretched over a standard clinical oxygen barb fitting.

Figure 9:
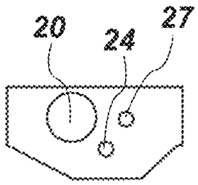
FIG. 9 shows a front view of one configuration of a connector housing with an optional third lumen as described herein.
Figure 7B:
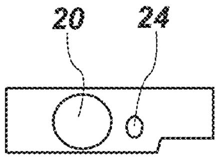
FIG. 7B shows a front view of one configuration of a connector housing as described herein.

In some configurations, a third lumen 27 may be provided (FIG. 9). The third lumen 27 may also have a diameter smaller than the diameter of the first lumen 20 to prevent the third lumen 27 from being connected to a standard oxygen barb fitting. The third lumen 27 may provide an additional lumen for drawing a sample of gas for analysis. For example, the third lumen may be used to draw a sample of exhaled CO 2 for end-tidal CO 2 analysis.

Figure 3:
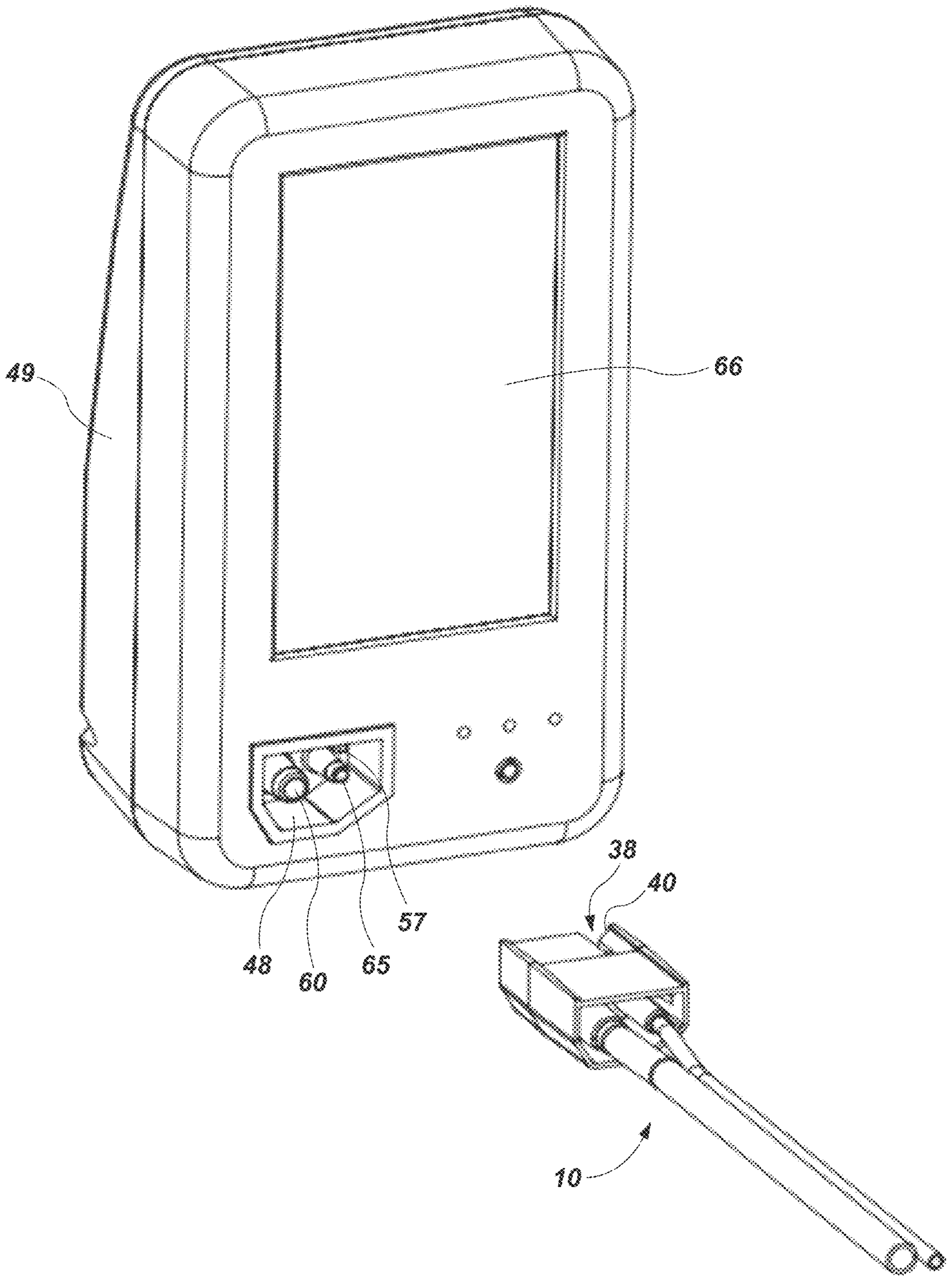
FIG. 3 shows a perspective view of the connector of FIG. 1 and an oxygen delivery control device to receive at least part of the connector.

The housing 15 of the connector 10 may substantially surround the first and second lumens 20, 24, and have one open side to be inserted into a receptacle 48 of an oxygen delivery control device 49 (FIG. 3). The housing 15 may be formed from a rigid or semi-rigid material to facilitate insertion into the oxygen delivery control device 49. The housing 15 may have a top surface extending from a first side to a second side. The top surface may be provided with a first top surface portion 30, or patient interface encoding portion 30, and a second top surface portion 35, or depth measurement insertion portion 35. An open slot 38 in the top surface of the housing 15 may separate the patient interface encoding portion 30 and the depth measurement insertion portion 35. While the patient interface encoding portion 30 and depth measurement insertion portion 35 are described as being located on a "top" surface of the housing 15, it will be appreciated that they may be located on any of the outer surfaces of the housing 15, such as the bottom, sides, etc. The patient interface encoding portion 30 may be on the same surface of the housing 15 as the depth measurement insertion portion 35, or it may be on a different surface. For example, the patient interface encoding portion 30 may be located on a side surface of the housing 15, and the depth measurement insertion portion 35 may be located on a top surface of the housing 15. Additionally, the connector 10 could be rotated at any angle with the corresponding receptacle placed on a similar angle.

Figure 4:
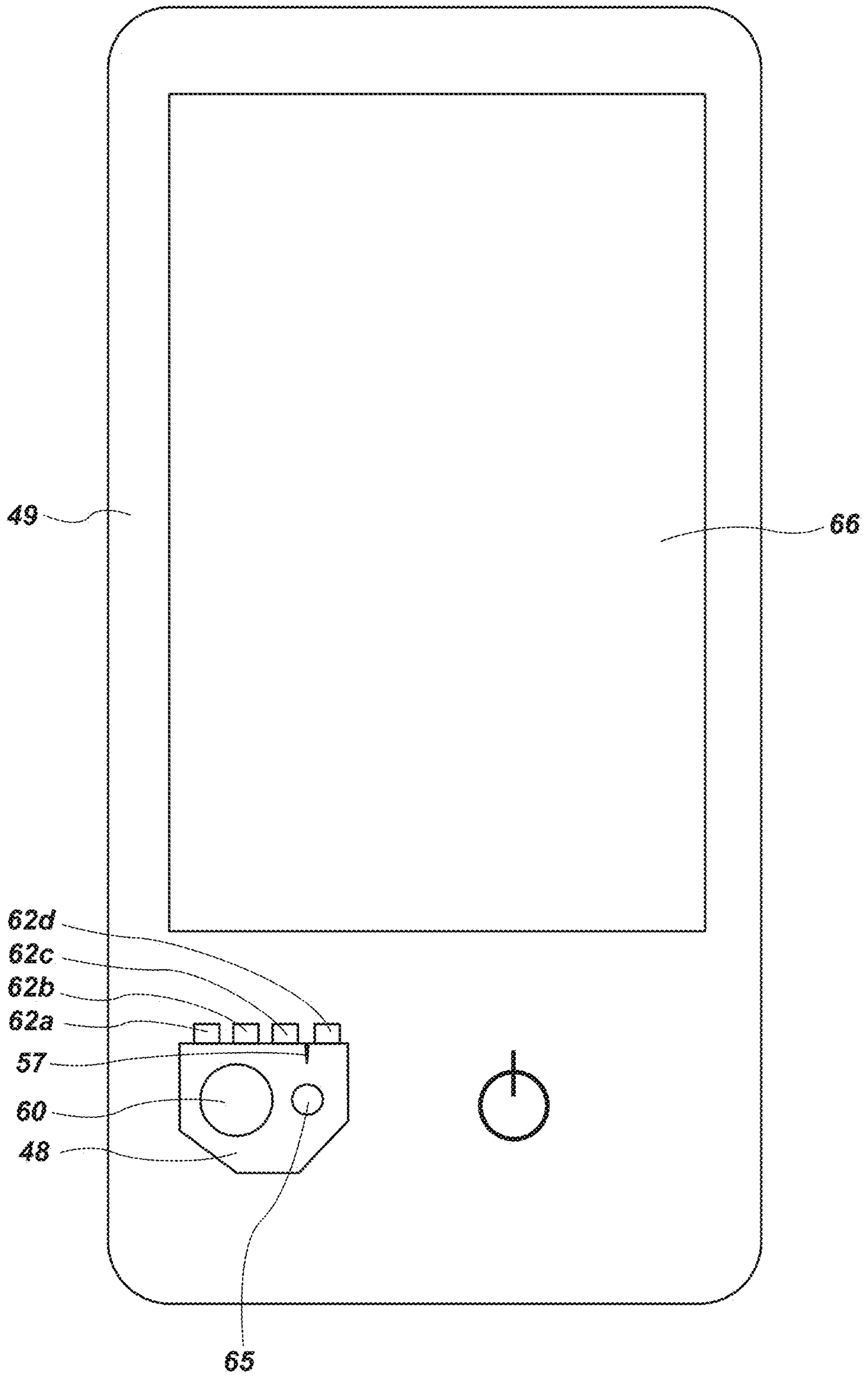
FIG. 4 shows a front, plan view of the oxygen delivery control device.
Figure 6A:
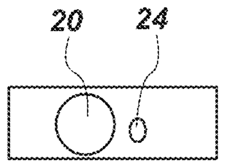
FIG. 6A shows a front view of one configuration of a connector housing as described herein.

The oxygen delivery control device 49 may comprise a receptacle 48 for receiving the housing 15 of the connector 10, the receptacle 48 having one or more readers for reading the information or data associated with the patient interface encoding portion 30, and/or depth measurement insertion portion 35. For example, the receptacle 48 may be provided with optical sensors (62*a*-*d* in FIG. 4) that are placed in the receptacle 48 proximal to the portions that would interface with the patient interface encoding portion 30 and the depth measurement insertion portion 35. The optical sensors may also be placed adjacent the receptacle 48. In one configuration (FIG. 4), the receptacle 48 may additionally include an optical isolation wall 57. The open slot 38 of the housing may receive the optical isolation wall 57 when the housing 15 is inserted into the receptacle 48 of the oxygen delivery control device 49. In this configuration, the receptacle 48 may include optical sensors in the top portion, with three optical sensors (62*a*-*c*) immediately above the receptacle 48 to one side of the optical isolation wall 57, and another optical sensor (62*d*) on the other side of the optical isolation wall 57. The receptacle 48 may also include a connector 60 for receiving the first lumen 20 and a smaller connector 65 for receiving the second lumen 24.

Turning back to FIGS. 1-2, there is shown a configuration in which the patient interface encoding portion 30 and the depth insertion measurement portion 35 of the housing 15 are not equal in size. In some configurations, the width of the patient interface encoding portion 30 may be larger than the width of the depth insertion measurement portion 35 (or vice versa). An open slot 38 in the top surface of the housing 15 may separate the patient interface encoding portion 30 (e.g., a first top surface portion) and the depth insertion measurement portion 35 (e.g., a second top surface portion), the open slot 38 configured to receive an optical isolation wall 57 of the oxygen delivery control device 49. In other words, the open slot 38 may be located towards one side of the top surface of the housing 15. For example, the open slot 38 may be positioned closer to the second side of the housing 15. This may allow the housing 15 of the connector 10 to only be inserted in one manner into the receptacle 48 and prevent upside-down insertion and other improperly aligned insertions, etc.

The patient interface encoding portion 30 of the housing 15 may include means to enable identification of information relating to the patient interface. For example, the patient interface encoding portion 30 may comprise at least one encoding optical reflectivity pad configured to enable identification of information relating to the patient interface. Other types of means for encoding information may also be used. The patient interface encoding portion 30 of the housing 15 may be marked/printed with a pattern that identifies information relating to the patient interface. The pattern may be comprised of multiple pads, each of which reflects light, for example, light in the visual and/or infrared wavelengths, in a variable amount (high reflectivity, low reflectivity, or intermediate). The arrangement of the reflectivity pads and the amount of reflectivity of the pads may corresponds to a code that allows the instrument to determine the specific type of patient interface that is plugged into the receptacle 48. The information relating to the patient interface may include, for example, type of patient interface, and/or a size of patient interface. Examples of types of patient interfaces include nasal cannulas, CPAP masks, auxiliary oxygen tubes, drug nebulizers, etc. The size of the patient interface may be, for example, adult, pediatric, neonatal, etc.

The information relating to the patient interface 47 may be read by one or more readers (such as optical sensors) located within the receptacle 48 of the oxygen delivery control device 49, and cause a software constraint relating to maximum oxygen flow, minimum oxygen flow, minimum and/or maximum mask pressure, maximum oxygen pulse frequency, etc., and/or another parameter. For example, if the oxygen delivery control device 49 reads the patient interface encoding portion 30 and determines the patient interface is a neonatal nasal cannula, a maximum oxygen flow rate may be set that prevents the patient from receiving an oxygen flow that is not safe. If the oxygen delivery control device 49 reads the patient interface encoding portion 30 and determines the patient interface is an adult CPAP mask the device will operate to control pressure within the mask rather than to control rate of oxygen flow through a cannula.

Figure 5A:
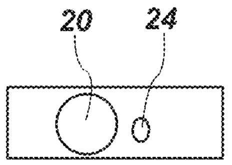
FIG. 5A shows a front view of one configuration of a connector housing as described herein.
Figure 5B:
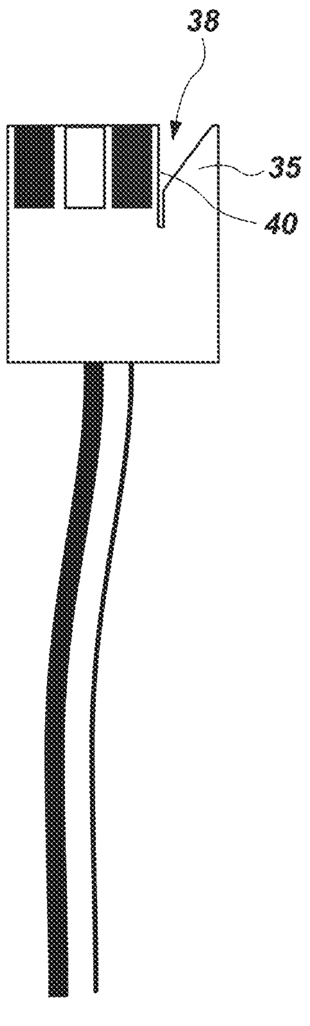
FIG. 5B shows a top view of the connector housing of FIG. 5A.
Figure 6B:
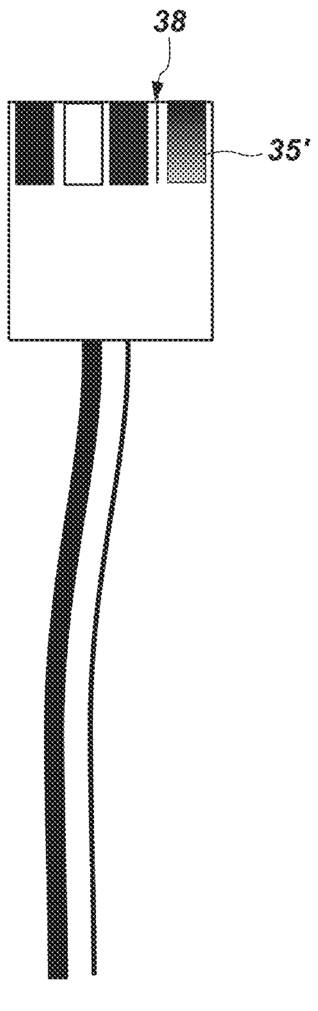
FIG. 6B shows a top view of the connector housing of FIG. 6A.
Figure 7A:
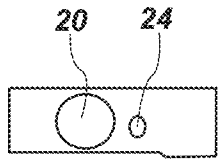
FIG. 7A shows a front view of one configuration of a connector housing as described herein.
Figure 8A:
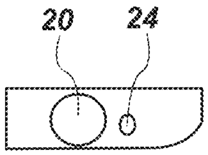
FIG. 8A shows a front view of one configuration of a connector housing as described herein.
Figure 8B:
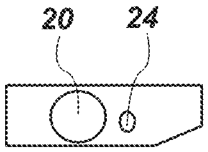
FIG. 8B shows a front view of one configuration of a connector housing as described herein.
Figure 8C:
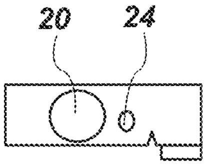
FIG. 8C shows a front view of one configuration of a connector housing as described herein.
Figure 7C:
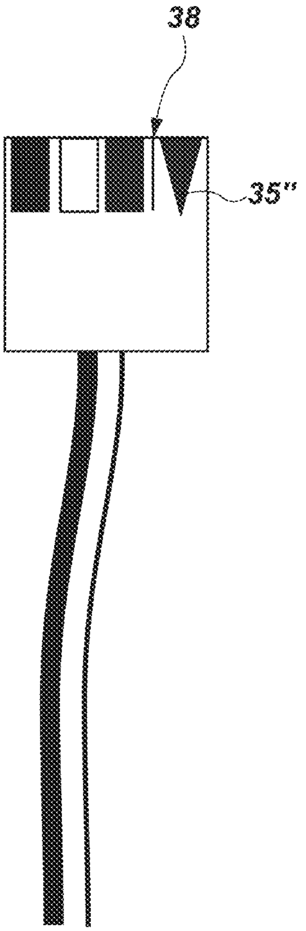
FIG. 7C shows a top view of the connector housing of FIGS. 7A and/or 7B.
Figure 8D:
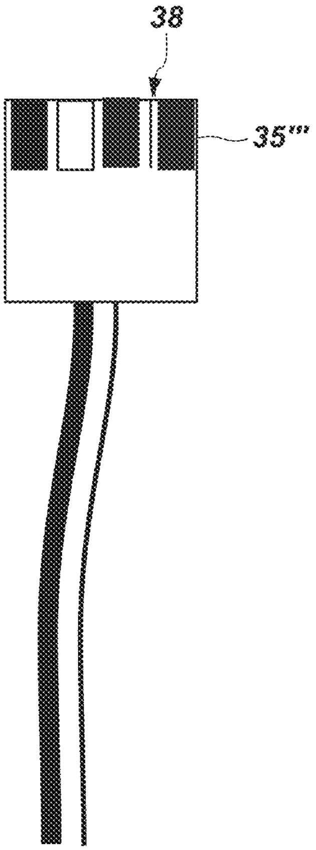
FIG. 8D shows a top view of the connector housing of FIGS. 8A, 8B, and/or 8C.

The depth measurement insertion portion 35 of the housing 15 of the connector 10 may include means to enable measurement of a depth of the housing 15 within the receptacle 48 of the oxygen delivery control device 49. For example, the means may include a triangle printed on the depth insertion portion (see FIG. 7C), a gradient printed on the depth insertion portion (FIG. 6B), an angled cut-away formed in the depth insertion portion (FIG. 5B showing chamfer 40), and a reflective pad placed on the depth insertion portion (FIG. 8D).

In some configurations, a chamfer 40 may be provided proximal to the open slot 38, the chamfer 40 configured to enable measurement of a depth of the housing 15 within the oxygen delivery control device 49. The chamfer 40 may allow an optical sensor to sense an increasing amount of reflectivity with insertion depth. The housing 15 may be molded such that a chamfer 40 would be located below an insertion depth optical sensor (62*d* in FIG. 4) of the receptacle 48. In this configuration, the amount of light that is reflected from the top surface of the housing 15 increases as the connector 10 is inserted as there is more material immediately below the sensor to reflect light. By removing the material of the housing 15 below the sensor, the reflection is decreased. The chamfer 40 may allow an optical detector to detect reflectance, and as the housing 15 is inserted into the receptacle 48, reflectance may increase with depth of insertion.

Other configurations may also be used such that the amount of reflected light is a function of the housing 15 insertion depth into the receptacle 48. For example, as seen in FIG. 7C, a continuously variable reflector may be incorporated by printing an arrow or triangle on the depth measurement insertion portion 35" such that when the housing 15 is inserted, the variable reflector is positioned under the depth sensing optical sensor of the receptacle 48. As the housing 15 is advanced into the receptacle 48, the amount of reflected light increases, or decreases, according to the depth of insertion. Various patterns may be printed on the depth measurement insertion portion 35 to achieve this effect. Examples of depth insertion sensing patterns include a white to black gradient pattern where the darkness of the print below the sensor becomes progressively darker or lighter from one extreme to the other extreme. Alternatively this could be done by blending colors (other than black or white) to create a gradient of reflectivity. Another method of creating a linearly increasing reflectivity pattern is to print an arrow or wedge of a dark area on a light background. Note that the logic could be inverted in each of these cases, for example the reflectivity would be greatest at the tip or at the base, as long as it is variable according to distance from the tip of the connector. A continuously variable reflective pad or substantially continuously variable reflective pad may also be provided. FIGS. 5A through 8E illustrate various reflectivity pads and chamfers that may be used to detect depth of the housing within the receptacle and type of patient interface.

Figure 8E:
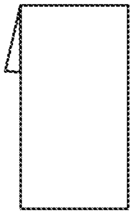
FIG. 8E shows a side view of the connector of FIG. 8C.

Another method of creating an insertion depth measurement with an optical sensor is to alter the distance between the sensor and the housing. The distance between the optical LED and detector pair and the reflective surfaced affects the reflected light signal. By adding a sloped surface on the top of the housing below the optical sensor, the amount of reflected light becomes a function of housing 15 insertion depth. That is, the sloped surfaced causes the distance between the optical sensor and the surface to change as the connector is inserted thereby changing the reflectivity. See FIG. 8E showing a side view of a housing 15 with a sloped surface on the depth measurement insertion portion 35'''. FIG. 8C shows a front view of the housing of FIG. 8E.

In use, a clinician may first select a connector with an appropriate patient interface (including, for example, patient size and type of interface). The clinician may then insert the housing of the connector into the receptacle of the oxygen delivery control device. The housing may only be able to be inserted into the receptacle in one manner due to the shape of the housing, the off-set optical isolation wall, etc. This may prevent a clinician from improperly inserting the housing of the connector into the receptacle and defeating the benefits of correct insertion. The first lumen 20 of the housing 15 may attach to the connector 60 of the receptacle 48, and the second lumen 24 may attach to the connector 65.

Upon insertion, the optical sensors of the oxygen delivery control device proximal to the receptacle may detect information relating to the patient interface, including the type of interface, size, etc. For example, optical sensors 62*a-c* of FIG. 4 may read reflectivity pads on the first top surface portion 30 of the top of the housing 15 of the connector 10. Upon detection, the optical sensors may send a signal relating to the patient interface to one or more processors. The one or more processors may then constrain the software of the oxygen delivery control device with parameters appropriate for the patient interface.

Additionally upon insertion, the optical sensor (for example, 62*d*) of the oxygen delivery control device proximal to the depth measurement insertion portion may measure the amount of reflectance and send a signal to one or more processors relating to the depth of the housing within the receptacle. The one or more processors may then determine if the depth is sufficient, and, if it is not, send an alarm to be outputted. For example, the one or more processors may compare the measured depth to a predetermined threshold depth and any depth that is less than the predetermined threshold may cause the alarm to be triggered. The alarm may include, for example, a visual alarm on the screen 66 of the oxygen delivery control device, and/or an audible alarm. The alarm may alert the clinician the housing of the connector is not inserted far enough and allow the clinician to correct. If the housing is inserted properly, the software may include an algorithm that continues to query the depth of the housing in the receptacle. If the housing becomes dislodged, the alarm may alert the clinician.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A connector for interfacing a patient interface to an oxygen delivery control device, the connector comprising:
- a first lumen for conveying oxygen from a source in connection with the oxygen delivery control device to the patient interface;
- a second lumen for monitoring respiratory pressures;
- a housing enclosing the first and second lumens, the housing having a top surface differentiated into multiple sections with varying widths, and including a slot in the top surface of the housing to engage an optical isolation wall of the oxygen delivery control device;
- wherein one of the multiple sections of the top surface comprises a reflective element to enable identification of information relating to the patient interface; and
- wherein another of the multiple sections of the top surface comprises a sloped feature proximal to the slot to facilitate engagement depth assessment of the housing within the oxygen delivery control device.

2. The connector of claim 1, wherein the first lumen is configured to receive a standard clinical oxygen barb connector.

3. The connector of claim 1, wherein the second lumen cannot receive a standard clinical oxygen barb connector.

4. The connector of claim 1, wherein the information relating to the patient interface comprises at least one of a type of patient interface and a size of patient interface.

5. The connector of claim 4, wherein the type of patient interface is selected from at least one of a nasal cannula, a CPAP mask, an auxiliary oxygen tube, and a drug nebulizer.

6. The connector of claim 4, wherein the size of patient interface is selected from at least one of adult, pediatric, and neonatal.

7. The connector of claim 1, wherein the reflective element is configured to cause a software constraint for the oxygen delivery control device when the reflective element is inserted into the oxygen delivery control device.

8. The connector of claim 7, wherein the software constraint comprises at least one of a maximum oxygen flow, a minimum oxygen flow, a minimum mask pressure, a maximum mask pressure, and a maximum oxygen pulse frequency.

9. The connector of claim 1, wherein the sloped feature is configured to cause an alarm output on the oxygen delivery control device when the sloped feature is partially inserted into the oxygen delivery control device for a predetermined amount of time.

10. The connector of claim 1, further comprising a third lumen, the third lumen having a diameter smaller than the diameter of the first lumen.

11. The connector of claim 10, the third lumen for drawing a sample of gas for analysis.

12. The connector of claim 11, wherein the gas includes exhaled $CO_2$.

13. The connector of claim 1, wherein the first and second lumens are formed from a flexible material.

14. The connector of claim 1, wherein the housing is formed of a rigid material.

15. A universal connector for connecting a patient interface to an oxygen delivery control device, the connector comprising:
- a housing with a top surface extending longitudinally from one end to the other, segmented by a slot in the top surface of the housing defining two distinct operational zones, (i) a patient interface encoding portion and (ii) a depth measurement insertion portion;
- the patient interface encoding portion of the housing equipped with an identifier mechanism for recognition and data correlation regarding the patient interface;
- the depth measurement insertion portion of the housing equipped with a geometric feature designed to assist in ascertaining an insertion depth of the connector in the oxygen delivery control device; and
- wherein the housing encloses a first lumen and a second lumen, the first lumen for conveying pressurized oxygen and the second lumen for pressure measurement at the patient interface, the second lumen having a smaller diameter than the first lumen.

16. The connector of claim 15, wherein the slot is positioned closer to one side of the housing.

17. The connector of claim 15, wherein the identifier mechanism for recognition and data correlation regarding the patient interface comprises means for optical detection.

18. The connector of claim 15, wherein the geometric feature designed to assist in ascertaining the insertion depth of the connector in the oxygen delivery control device comprises at least one of: a triangle printed on the depth measurement insertion portion, a gradient printed on the depth insertion portion, an angled cut-away formed in the depth insertion portion, and a reflective pad placed on the depth insertion portion.

19. A method for connecting a patient interface to an oxygen delivery control device, the method comprising:
- providing the connector of claim 15,
- providing the oxygen delivery control device, the oxygen delivery control device comprising a receptacle to receive at least a portion of the housing of the connector, the receptacle having an isolation feature;
- engaging the connector with the receptacle of the oxygen delivery control device; and
- wherein the method leverages encoded features on the connector for automated system recognition and operational parameter adjustment based on detected interface data.

* * * * *